United States Patent
Hackett et al.

[11] Patent Number: 5,555,893
[45] Date of Patent: Sep. 17, 1996

[54] SHAFT MOVEMENT CONTROL APPARATUS

[75] Inventors: Steven S. Hackett, Maple Grove; Roger N. Hastings, Burnsville; Arnold W. Thornton, Roseville; Darlene A. Thometz, Maple Grove; Kenneth R. Larson, Bloomington; Scott P. Thorne, Waite Park; John W. Humphrey, Eden Prairie, all of Minn.

[73] Assignee: SciMed Life Systems, Inc., Maple Grove, Minn.

[21] Appl. No.: 48,492

[22] Filed: Apr. 16, 1993

Related U.S. Application Data

[63] Continuation-in-part of Ser. No. 929,083, Aug. 12, 1992.

[51] Int. Cl.$^6$ ....................................................... A61B 5/00
[52] U.S. Cl. ............................................................. 128/772
[58] Field of Search ................................... 128/657, 658, 128/772; 604/95, 280, 284

[56] References Cited

U.S. PATENT DOCUMENTS

| | | |
|---|---|---|
| 3,358,676 | 12/1967 | Frei et al. . |
| 3,674,014 | 7/1972 | Tillander ................................ 128/657 |
| 3,722,505 | 3/1973 | Kolin . |
| 3,941,119 | 3/1976 | Corrales . |
| 3,961,632 | 6/1976 | Moossun . |
| 4,054,128 | 10/1977 | Seufert et al. . |
| 4,077,412 | 3/1978 | Moossun . |
| 4,134,405 | 1/1979 | Smit . |
| 4,244,362 | 1/1981 | Anderson ................................ 128/772 |
| 4,249,536 | 2/1981 | Vega . |
| 4,315,509 | 2/1982 | Smit . |
| 4,671,287 | 1/1987 | Fiddian-Green . |
| 4,726,369 | 2/1988 | Mar ........................................ 128/303 |
| 4,784,117 | 11/1988 | Miyazaki .................................... 128/4 |
| 4,784,646 | 11/1988 | Feingold . |
| 4,790,809 | 12/1988 | Kuntz . |

(List continued on next page.)

FOREIGN PATENT DOCUMENTS

| | | |
|---|---|---|
| 0416734A1 | 7/1990 | European Pat. Off. . |
| 0415332A1 | 8/1990 | European Pat. Off. . |
| 0409372A1 | 1/1991 | European Pat. Off. . |
| 0415332 | 3/1991 | European Pat. Off. . |
| 2245495 | 1/1992 | United Kingdom . |
| WO81/02109 | 8/1981 | WIPO . |

OTHER PUBLICATIONS

J. Driller, W. Casarella, T. Asch, S. K. Hilal; *The POD Bronchial Catheter*, IEEE Transactions on Mangetics, vol. Mag–6, No. 2, pp. 353–355, Jun. 1970.

A. Snider; *New Techniques Used in Lung Biospy*, The Washington Post, p. E16, Thursday, Dec. 4, 1969.

H. Tillander; *Selective Angiography with a Catheter Guided by a Magnet*, IEEE Transactions on Magnetics, vol. Mag–6, No. 2, pp. 355–358, Jun. 1970.

D. Montgomery and R. Weggel; *Magnetic Forces for Medical Application*, IEEE Transactions on Magnetics, p. 374, Jun. 1970.

D. Montgomery, J. Hale, N. Pierce and S. Yodh; *A Magnetically Guided Catheter System for Intracranial Use in Man*, IEEE Transactions on Magnetics, pp. 374–375, Jun. 1970.

Primary Examiner—Max Hindenburg
Attorney, Agent, or Firm—Nawrocki, Rooney & Sivertson

[57] ABSTRACT

The present invention is a device and method for controlling longitudinal movement of a tube relative to a shaft slidably disposed within the tube, especially in the catheterization of a patient. An operative segment on the shaft cooperates with an ancillary tool to create a coupling force field between the shaft and the tool. The tube can then be moved over the shaft while the coupling force field operates through the tube to restrict the movement of the shaft. In preferred embodiment, the shaft is a guide wire and the tube is a catheter with a lumen for slidably receiving the guide wire, while the coupling force field is created magnetically. In one embodiment, the operative segment is borne on a short guide wire extension which is selectively securable to a standard guide wire.

14 Claims, 14 Drawing Sheets

U.S. PATENT DOCUMENTS

| | | | |
|---|---|---|---|
| 4,804,054 | 2/1989 | Howson et al. . | |
| 4,809,713 | 3/1989 | Grayzel . | |
| 4,875,489 | 10/1989 | Messner et al. | 128/657 |
| 4,922,923 | 5/1990 | Gambale et al. . | |
| 5,020,367 | 6/1991 | White | 73/319 |
| 5,035,686 | 7/1991 | Crittenden et al. . | |
| 5,117,838 | 6/1992 | Palmer et al. . | |
| 5,161,534 | 11/1992 | Berthiaume | 128/657 |
| 5,234,407 | 8/1993 | Teirstein et al. | 604/53 |
| 5,257,636 | 11/1993 | White | 128/897 |
| 5,269,759 | 12/1993 | Hernandez et al. | 128/772 |

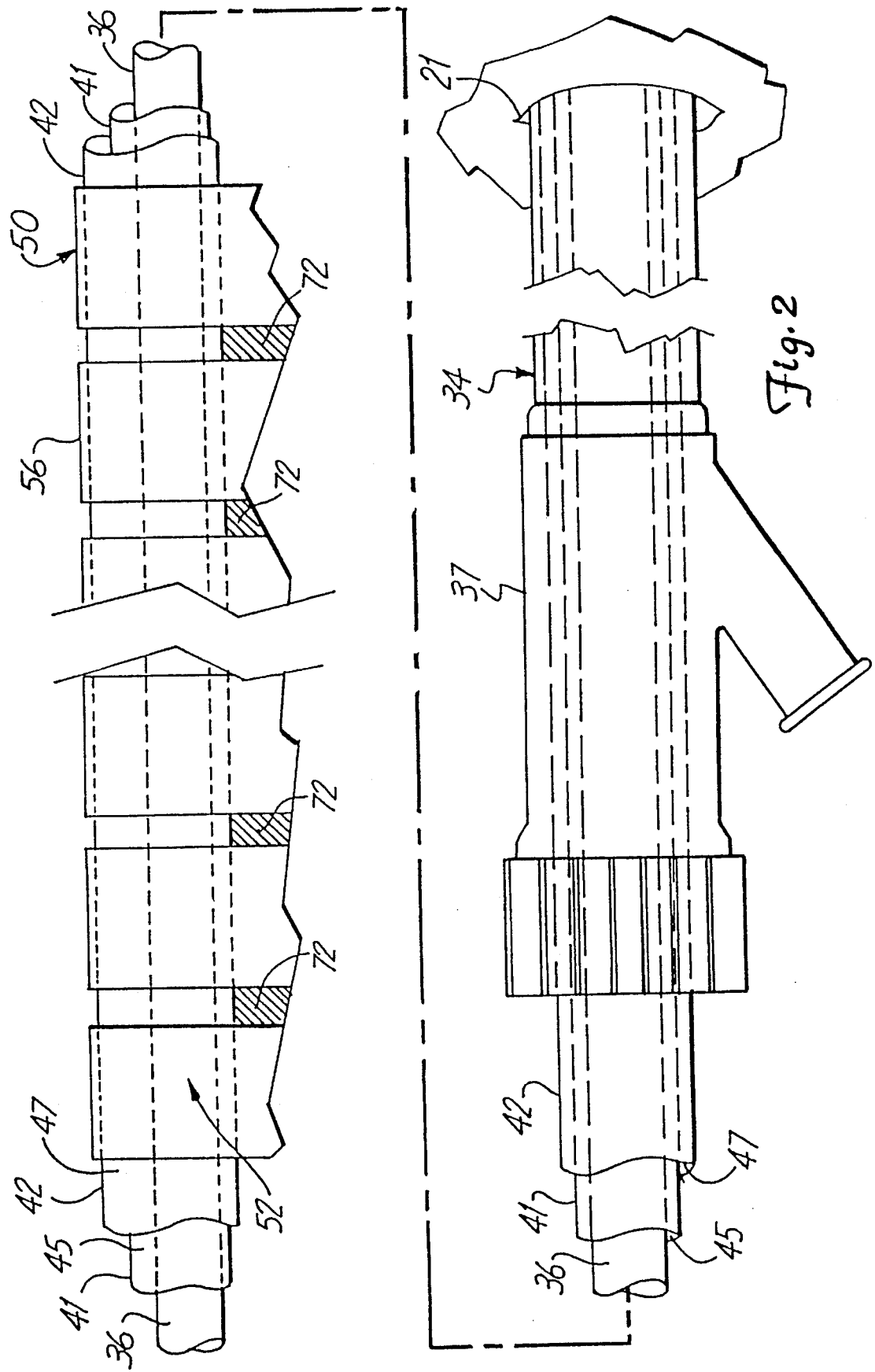

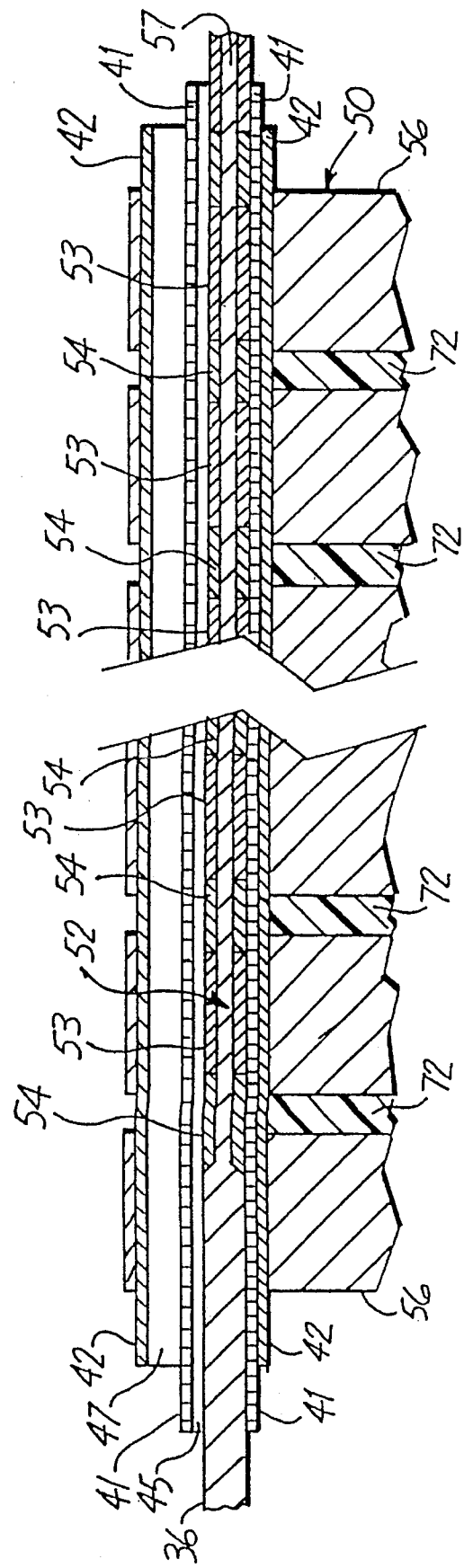

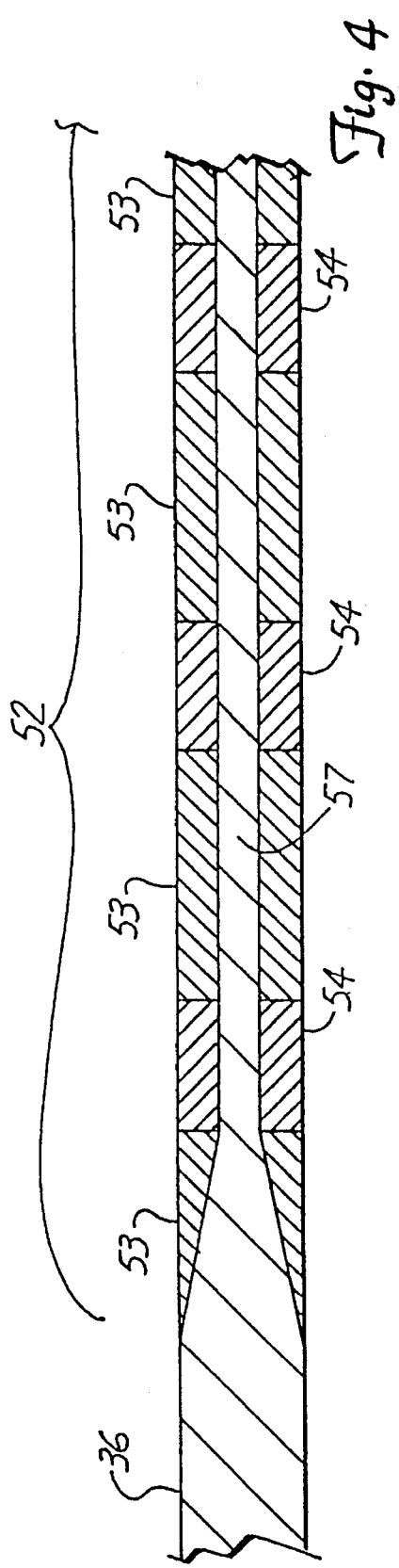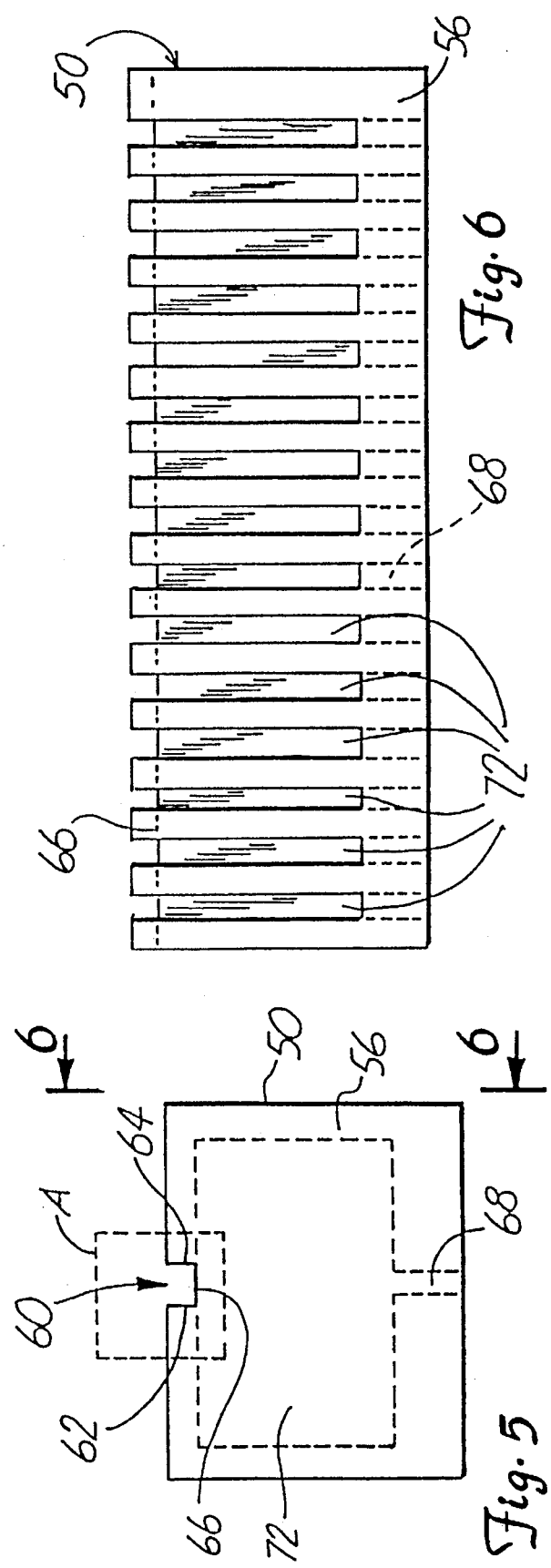

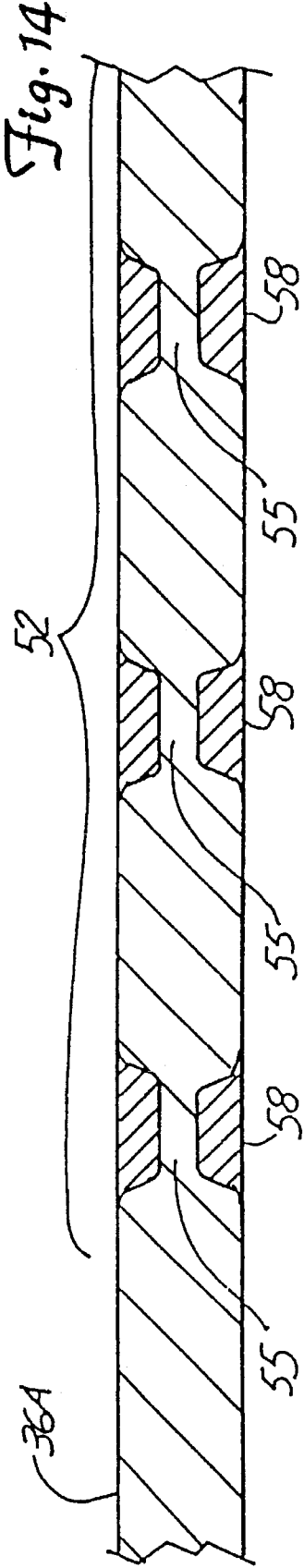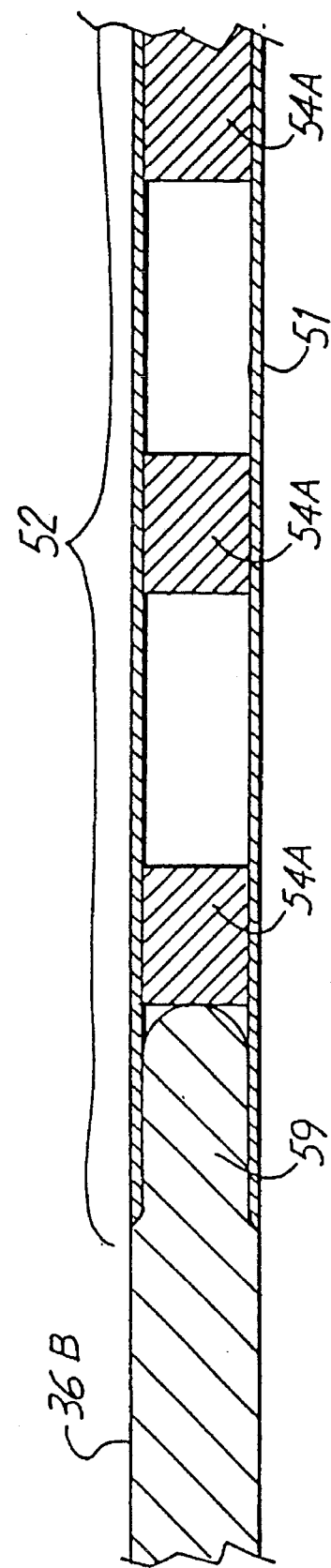

SHAFT MOVEMENT CONTROL APPARATUS

This application is a continuation-in-part of U.S. Ser. No. 07/929,083, filed Aug. 12, 1992.

BACKGROUND OF THE INVENTION

The present invention relates to the field of medical devices, particularly catheters. In particular, the present invention relates to a method and device for controlling movement of an elongate shaft for use in the catheterization of a patient, where a portion of the shaft is inserted within the patient.

Angioplasty has gained wide acceptance in recent years as an efficient and effective method for treating types of vascular diseases. In particular, angioplasty is widely used for opening stenoses in the coronary arteries, although it is also used for treatment of stenoses in other parts of the vascular system.

The most widely used form of angioplasty makes use of a dilatation catheter which has an inflatable balloon at its distal end. Using fluoroscopy, the physician guides the dilatation catheter through the vascular system until the balloon is positioned across the stenosis. The balloon is then inflated by supplying a fluid under pressure through a inflation lumen to the balloon. The inflation of the balloon causes stretching of the artery and pressing the lesion into the artery wall to re-establish acceptable blood flow through the artery. In some angioplasty procedures, it may be desirable to use a series of dilatation catheters having different sizes or balloon configurations.

One type of dilatation catheter has a guide lumen provided therein so that a guide wire can be used to establish the path through the stenosis. The dilatation catheter is then advanced over the guide wire until the balloon is positioned across the stenosis. The use of a guide wire enables the catheter to be advanced through the blood vessel relatively quickly, thereby reducing the time required for the procedure.

A "standard" guide wire for use in coronary angioplasty is about 175 cm long while a typical coronary angioplasty catheter is about 150 cm long. When the catheter is in place over the guide wire for use, a portion of the guide wire protrudes proximally from the catheter. The protruding portion enables the guide wire to be manipulated by a physician.

In some instances, it may be desirable to exchange one dilatation catheter (already on the guide wire) for a second dilatation catheter. It is usually preferred that the catheter be removed in a manner which enables the guide wire to remain in place in the blood vessel so that the succeeding catheter may be inserted into the blood vessel, over the guide wire already in place, and guided to the stenosis in the blood vessel. To maintain a guide wire in place while withdrawing the catheter, the guide wire must be gripped at its proximal end to prevent it from being pulled out of the blood vessel with the catheter. The catheter, however, is longer than the proximal portion of the guide wire which protrudes out the patient. Thus, before the catheter is fully withdrawn, it completely covers the proximally extending portion of the guide wire. As a result, there was no means by which a standard guide wire can be held in place to prevent it from being withdrawn together with the catheter. To withdraw the catheter while leaving the guide wire in place, a guide wire with a longer effective length was required.

One means for addressing this difficulty is to use an exchange wire when performing a catheter exchange. An exchange wire may be used initially or may be exchanged for a standard guide wire already in place in the patient. An exchange wire typically is much longer (e.g., 300 cm) than the typical or standard guide wire. The additional length of the exchange wire results in a proximally protruding portion which is longer than the length of the catheter to be removed. When a catheter is removed, some part of the proximally protruding portion of the exchange wire is always exposed to provide a means by which the exchange wire can be gripped and its position in the blood vessel maintained. The succeeding catheter is then inserted into the patient over the exchange wire.

It is generally recognized as undesirable to insert, advance and withdraw a series of guide wires during these types of procedures. Repeated guide wire insertions increase the risk of injury to the patient and also increase the time required for the procedure. It also requires exposure of the patient to additional radiation because of the additional fluoroscopy which is required to properly place the successive guide wires across the stenosis. In addition, long exchange wires are cumbersome and difficult to handle while maintaining the guide wire in place across the stenosis.

Techniques to eliminate the need to change guide wires have been proposed. One solution is the use of a guide wire extension which is attached to the proximal end of the guide wire while the guide wire remains in place in the patient. The guide wire extension effectively increases the length of the guide wire to that of an exchange guide wire. While the technique substantially shortens the duration of the procedure because the extension can be attached at the proximal end of the guide wire much faster than an exchange of guide wires can be performed, the extended guide wire is still cumbersome as the physician is required to handle an extended length of a guide wire outside of the patient during at least a portion of the procedure.

One means for catheter exchange without lengthening the guide wire is by use of a balloon catheter with a guide wire lumen located only adjacent the distal end of the catheter. With this configuration, the guide wire is external to the balloon catheter except adjacent the distal end of the balloon catheter. This catheter arrangement allows the catheter to be withdrawn over the guide wire without requiring the physician to completely release the guide wire until the distal end of the catheter is outside of the patient's body. The guide wire lumen on the catheter is shorter than the length of exposed guide wire, which allows at least some portion of the proximal end of the guide wire to be exposed at all times so that it can be grasped and its position relative to the stenosis can be maintained during removal of the catheter.

Another means for exchanging a catheter without the use of an extended guide wire is to engage the guide wire at a point distally of the catheter and hold it in place relative to the stenosis. This has been done by providing an inflatable guide wire holding balloon which is adapted to be inflated only within a guide catheter. In this arrangement, the dilatation catheter in the patient is withdrawn over the guide wire and inside of the guide catheter a short distance. The guide wire holding balloon is aligned distally relative to the dilatation catheter and is then inflated, thereby "trapping" the guide wire against an inner wall of the guide catheter (and constraining the guide wire from longitudinal movement relative to the guide catheter). The dilatation catheter is then withdrawn over the guide wire (the proximal end of the guide wire can be released) and a second dilatation catheter is placed on the guide wire and advanced along the guide wire to the point where the guide wire is trapped against the guide catheter wall. The guide wire holding balloon is then deflated and the physician advances the second dilatation catheter along the guide wire to the stenosis to continue the procedure. It also has been disclosed that mechanical means such as a wire snare be used within a guide catheter to secure the guide wire thereto, instead of a balloon.

While arrangements have been proposed to facilitate catheter exchanges in guide wire catheter systems without the need for a long guide wire length, they require a modified catheter (no full-length guide wire lumen) or additional components within the patient (e.g., balloon for trapping guide wire within guide catheter). It is desired to devise an arrangement which allows catheter exchanges over a standard length guide wire using a catheter having a full-length guide wire lumen.

SUMMARY OF THE INVENTION

The present invention is a method and device for controlling movement of a shaft for use in the catheterization of a patient where a distal portion of the shaft is inserted within the patient. The present invention is also useful for facilitating movement of a tube relative to a shaft extending through the tube, where distal portions of both the tube and the shaft are inserted within a patient.

The device of the present invention includes two pieces used in conjunction with each other. The first piece is an operative segment on the shaft. The second piece is an ancillary tool which, when positioned adjacent the operative segment on the shaft, cooperates with the operative segment to create a coupling force field between the operative segment and the tool, thus coupling the tool and the shaft together. The force created between the two pieces is strong enough to maintain the position of the shaft relative to the tool when the tube is aligned over the operative segment of the shaft.

In one preferred embodiment, the present invention is used to facilitate catheter exchanges in a guide wire catheter system without the need for a long guide wire length. In this preferred embodiment, the shaft is a guide wire, and the tube is a catheter with a lumen for slidably receiving the guide wire. The coupling force field between the operative segment on the guide wire and the tool is created by magnetism and is strong enough to maintain the tool and the guide wire in a coupled relation when the catheter is aligned over the operative segment on the guide wire and the catheter is moved longitudinally relative to the guide wire. The materials used to create the magnetic coupling force may be permanent magnets or magnetically permeable material.

The present invention is ideally suited for facilitating catheter exchanges without the need for a long guide wire length or a modified catheter. When a guide wire catheter system utilizing the present invention is pre-inserted within the vessel of a patient, the original catheter may be exchanged for a second catheter by simply aligning the operative segment on the guide wire with the tool to create the coupling force field; withdrawing the original catheter proximally past the tool and over the guide wire (which is held stationary relative to the tool) until the catheter is free of the guide wire; aligning the second catheter over the guide wire; and advancing the second catheter past the tool and over the guide wire until the second catheter is properly positioned. A handle, which couples fixedly to the tool and slidably to the catheter assembly, provides for ease of operation. The catheter assembly is stabilized within the tool through the use of a geometrically configured catheter receiving notch.

BRIEF DESCRIPTION OF THE DRAWINGS

The invention will be further described with reference to the accompanying drawings where like numbers refer to like parts in several views and wherein:

FIG. 2 is an enlarged view in side elevation of one embodiment of the present invention which shows guide wire captivation.

FIG. 3 is a sectional view of the captivation tool in FIG. 2.

FIG. 4 is a detail sectional view of an operative segment of a guide wire which is one preferred embodiment of the present invention.

FIG. 5 is a view in end elevation showing one preferred embodiment of the present invention.

FIG. 6 is a view in side elevation along line 6—6 in FIG. 5.

FIG. 8 shows the catheter and guide wire pre-inserted in a vessel of a patient, with the operative segment on the guide wire disposed within the proximal end of the dilatation catheter.

FIG. 9 shows the tool being placed over the operative segment of the guide wire.

FIG. 10 shows the dilatation catheter being withdrawn over the guide wire and past the tool.

FIG. 11 shows the dilatation catheter external from the patient's body with the tool adjacent the operative segment on the guide wire.

FIG. 12 shows the dilatation catheter external to the patient's body with the tool removed from adjacent the guide wire.

FIG. 13 shows the guide wire remaining in place in the vessel of the patient with the tool and dilatation catheter removed.

FIG. 14 is a detail sectional view of an operative segment of a guide wire which is another preferred embodiment of the present invention.

FIG. 15 is a detail sectional view of an operative segment of a guide wire which is another preferred embodiment of the present invention.

While the above identified drawing features set forth preferred embodiments, other embodiments of the present invention are also contemplated, as noted in the discussion. This disclosure presents illustrative embodiments of the present invention by way of representation and not limitation. It should be understood that numerous other modifications and embodiments can be devised by those skilled in the art which fall within the scope and spirit of the principles of this invention. It should be noted that the figures have not been drawn to scale as it has been necessary to enlarge certain portions for clarity.

DETAILED DESCRIPTION OF THE PREFERRED EMBODIMENTS

The present invention is a method and device for controlling movement of an elongated shaft in the catheterization of a patient, where a portion of the shaft is inserted within the patient. More precisely, the present invention is a method and device for controlling the movement of an elongated shaft extending through an elongated tube, wherein a portion of both the tube and shaft are inserted within the patient. In one preferred embodiment, the shaft is a guide wire and the tube is a catheter with a lumen for slidably receiving the guide wire.

Figure 1:
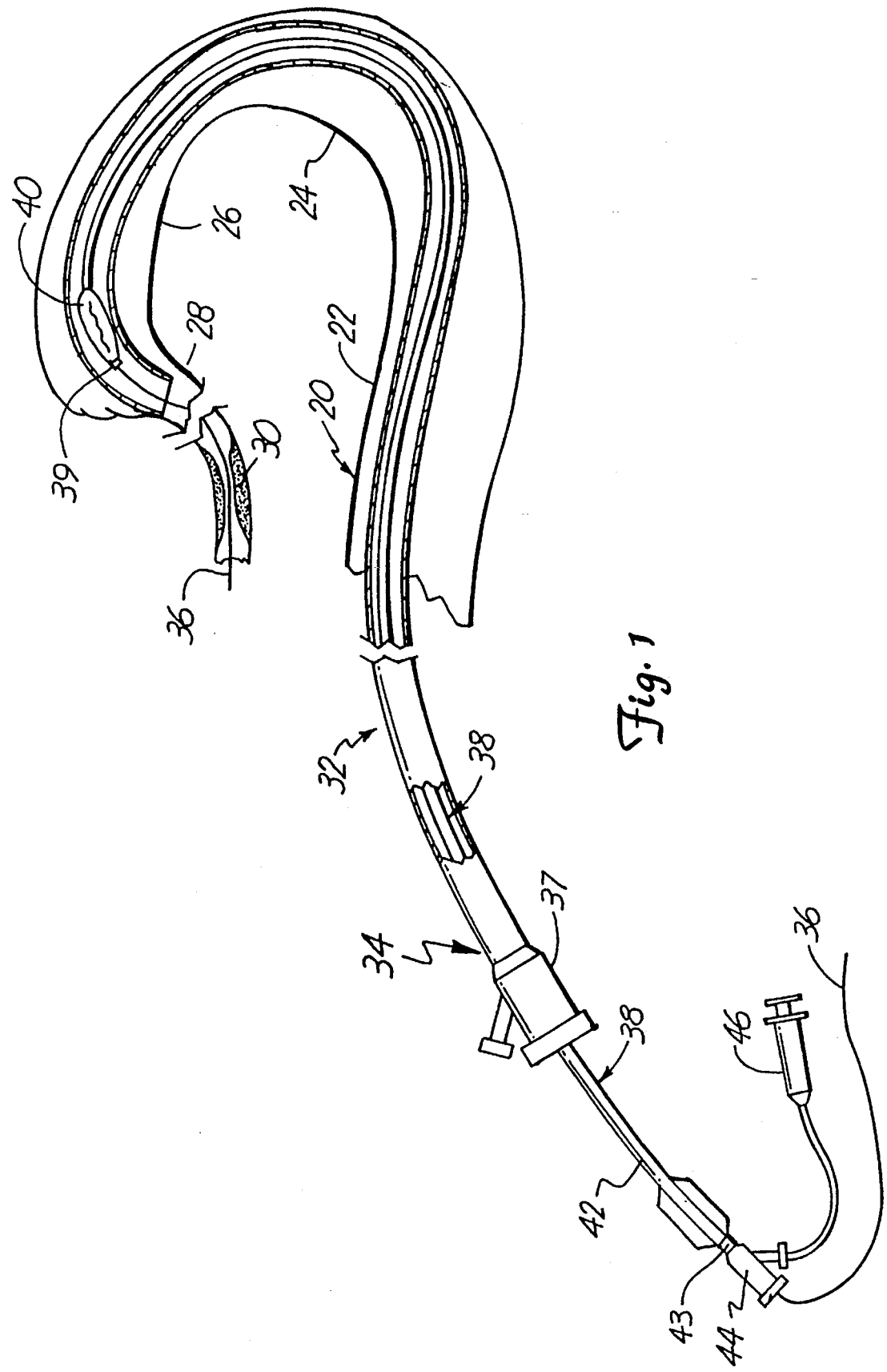
FIG. 1 is a diagrammatic view of an angioplasty catheter system in the vascular system of a patient.

A vascular system 20 and an angioplasty catheter system 32 are shown in FIG. 1. In an angioplasty procedure, entry into the vascular system 20 is typically through the femoral artery in the thigh (as schematically shown at 21 in FIGS. 2 and 8). A distal portion of the vascular system 20 includes a descending aorta 22, an aortic arch 24, and an ascending aorta 26. Extending from the ascending aorta 26 is a coronary artery 28, in which a stenosis 30 is formed.

The angioplasty catheter system 32 includes a guide catheter 34, a guide wire 36 extending through the guide catheter 34, and a dilatation catheter 38 with an inflatable balloon 40 mounted at a distal end 39 of a main tubular shaft 42 of the dilatation catheter 38. The dilatation catheter 38 is designed for use in conjunction with a guide wire, and has a guide wire lumen 45 (FIGS. 2, 3 and 7) extending along its entire length. The dilatation catheter 38 also has an inflation lumen 47 extending therethrough. The dilatation catheter 38 may be a dual lumen or coaxial lumen structure. In a coaxial arrangement (as shown), the inflation lumen 47 is provided between the outer main shaft 42 and an inner tubular shaft 41 disposed coaxially within the outer shaft 42. The guide wire lumen 45 is thus defined by the interior of the inner tubular shaft 41.

As illustrated in FIG. 1, a proximal portion of the guide wire 36 protrudes proximally out of a proximal end 43 of the dilatation catheter 38 and a proximal portion of the dilatation catheter 38 protrudes proximally out of a Y-adaptor 37 connected to a proximal end of the guide catheter 34. An inflation manifold 44 is connected to the proximal end 43 of the dilatation catheter 38 for facilitating inflation of the balloon 40. An inflation device 46 for inflating the balloon 40 is in fluid communication with the balloon 40 via the inflation manifold 44 and the inflation lumen 47.

The basic angioplasty procedure consists of inserting the guide catheter 34 into the vascular system 20 at the femoral artery. The guide catheter 34 is advanced through the vascular system 20 until a distal end of the guide catheter 34 is adjacent the mouth of the coronary artery 28 as shown in FIG. 1. Next, the distal end 39 of the dilatation catheter 38 is loaded onto and over a proximal end of the guide wire 36 and advanced over the guide wire 36 until the distal end 39 of the dilatation catheter 38 is adjacent a distal end of the guide wire 36. Then, the assembled combination of the guide wire 36 and the dilatation catheter 38 is inserted into the proximal end of the guide catheter 34 and advanced distally therethrough, retracing the already established path of the guide catheter 34 through the patient's vascular system 20. The guide wire 36 and the dilatation catheter 38 combination typically is advanced distally until adjacent the distal end of the guide catheter 34. The distal tip of the guide wire 36 is then advanced separately and manipulated into the artery tree to and across the stenosed artery. The dilatation catheter 38 is then advanced over the guide wire 36 to position the balloon 40 across the stenosis 30. The balloon 40 is inflated to dilate the stenosis 30 to re-establish acceptable blood flow through the artery.

However, sometimes the dilatation catheter 38 must be exchanged for another dilatation catheter to complete the angioplasty procedure. When exchanging the dilatation catheter 38 for another catheter, it is desirable to hold the guide wire 36 in place across the stenosis 30 during withdrawal of the dilatation catheter 38 (and advancement of the next catheter) to eliminate the need to re-establish the position of the guide wire 36 by retracing the tortuous path to the stenosis 30 after the dilatation catheter 38 is exchanged. Maintaining the guide wire 36 in place after an initial dilatation also provides the physician with a path through the stenosis 30 in case of an abrupt closure of the vessel.

The present invention facilitates holding the guide wire 36 in place across the stenosis 30 without requiring an exchange wire, an extension wire or additional intravascular devices to accomplish the dilatation catheter exchange over the guide wire 36. In one form of the present invention, means are provided proximally of the guide catheter Y-adaptor 37 to cooperate with the guide wire 36 for maintaining the position of the guide wire 36 across the stenosis 30. One preferred embodiment of the present invention, as shown in FIGS. 2–7, employs a captivation tool 50 which cooperates with an operative segment 52 of the guide wire 36 to create a coupling force field between the tool 50 and the operative segment 52. The coupling force field is defined by an energy field (such as a magnetic field). The force generated by the field is strong enough to maintain the position of the guide wire 36 relative to the tool 50 when the dilatation catheter 38 is aligned over the operative segment 52 of the guide wire 36, and particularly when the dilatation catheter 38 is moved over the guide wire 36. As shown in FIG. 2, the operative segment 52 of the guide wire 36 is located on a proximal portion of the guide wire 36 and is positioned so that the operative segment 52 is located some distance beyond the proximal end of the guide catheter Y-adaptor 37.

As seen in FIG. 3, the operative segment 52 of the guide wire 36 includes a plurality of magnetically permeable segments 54 secured on the guide wire 36 at locations along the guide wire 36. (Examples of suitable magnetically permeable materials are Rodar, manufactured by T. N. Wilbur B. Driver Company and available in tube form from Uniform Tubes of Collegeville, Pa.; Hiperco Alloy 50, manufactured by Carpenter Steel of Reading, Pennsylvania; Permendur or 2 V Permendur, listed as high permeable magnetic materials having large saturation flux densities in the CRC Handbook of Chemistry and Physics, 47th ed.; or any other material with a suitably large residual induction). In this embodiment, as seen in FIGS. 3 and 4, the operative segment 52 includes a plurality of magnetically permeable segments 54 secured about a reduced diameter portion 57 of guide wire 36. Non-magnetically permeable segments 53 are disposed between and about each of the magnetically permeable segments 54, respectively. In all embodiments of the operative segment 52 on the guide wire 36, the outside diameter of the operative segment 52 stays essentially the same as the outside diameter of the guide wire 36, and the transitions between magnetically permeable and non-magnetically permeable materials are smooth.

Figure 7:
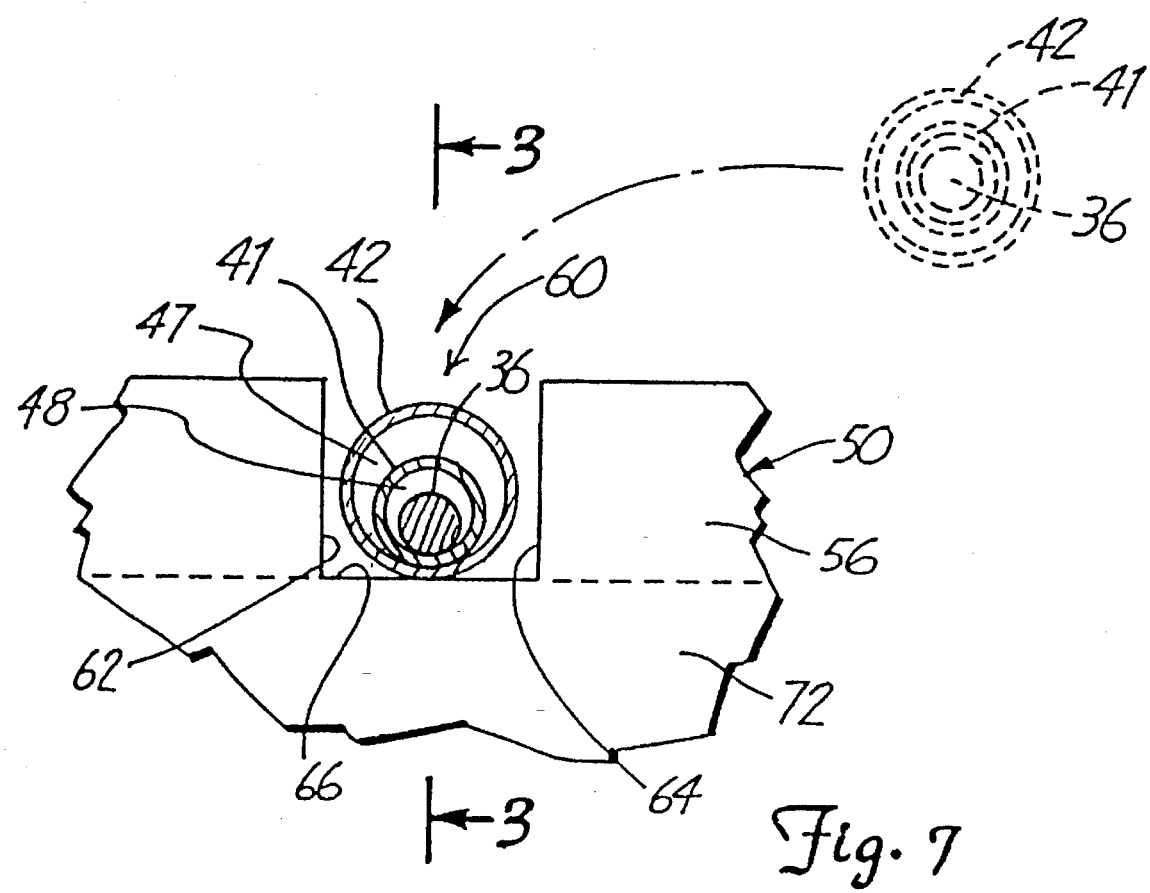
FIG. 7 is an enlarged fragmentary detail of portion A in FIG. 5 illustrating the placement of a catheter assembly, shown in section, into the tool housing.

As seen in FIGS. 5–7, the captivation tool 50 includes a housing member 56. The housing member 56 includes a longitudinal slot 60 defined by a pair of side slot surfaces 62 and 64, and a bottom slot surface 66. The slot 60 provides a space with sufficient size to slidably receive the dilatation catheter 38 and allow the dilatation catheter 38 to longitudinally pass freely through the slot 60, yet still restrict lateral movement of the dilatation catheter 38 between the slot surfaces 62, 64, and 66.

The housing member 56 also includes a plurality of rectangular-shaped magnetic sections 72 (shown in phantom in FIG. 5) which have exposed surfaces at bottom slot surface 66. As best seen in FIG. 6, the magnetic sections 72 are provided at longitudinally spaced locations along the housing member 56 corresponding to the spacing of the magnetically permeable sections 54 on the guide wire 36. The magnetically permeable sections 54 on the guide wire 36 and the magnetic sections 72 in the housing member 56 are spaced such that they can be aligned across from each other as shown in FIG. 3. Although the material of the bottom slot surface 66 alternates between the housing member 56 and the magnetic sections 72, the bottom slot surface 66 is smooth. The magnetic sections 72 are preferably made from a strong magnetic material with a large cohesive force (such as neodymium boron iron) that can hold a magnetization through a relatively thin section.

The size and spacing of the magnetic sections 72, as well as the size and spacing of the magnetically permeable sections 54 of the operative segment 52 on the guide wire 36, are chosen to maximize the longitudinal attractive force on the guide wire 36 while minimizing the radial attractive force on the guide wire 36. The net force for maintaining the position of the guide wire 36 relative to the tool 50 is governed by the equation:

$$F_{net}=F_L-\mu F_R$$

where $F_{net}$ is the net force available to maintain the position of the guide wire 36, $F_L$ is the longitudinal force of attraction between the tool 50 and the operative segment 52 on the guide wire 36, $F_R$ is the radial force of attraction between the tool 50 and the operative segment 52, and $\mu$ is the friction coefficient between the guide wire 36 and the dilatation catheter 38. Thus, to obtain optimum performance from the device, it is desirable to maximize the force $F_L$ and minimize the force $F_R$ and the friction coefficient $\mu$. The friction coefficient $\mu$ may be reduced through the use of lubricous coatings and materials, and the attractive forces $F_L$ and $F_R$ may be optimized through the use of mathematical modeling techniques known in the art. For example, positioning the magnetic sections 72 in the tool 50 such that the polarity of the magnetic sections 72 alternates between magnetic sections 72 reduces the radial attractive force $F_R$. Such alternation increases the total effective magnetic field, thereby increasing the longitudinal holding force. The total coupling force between the operative segment 52 and the tool 50 is proportional to the number of magnetic sections 72 in the tool 50.

In one preferred embodiment, the guide wire 36 has an outside diameter of 0.018 inches. The operative segment 52 has a length of approximately 10 inches with approximately 50 magnetically permeable sections 54, each having a length of 0.1 inch, separated by non-magnetically permeable sections 53 with a length of 0.1 inch. A non-operative segment approximately 2 inches long is attached to the proximal end of the operative segment 52. The tool 50 is approximately 4.0 inches long, 1.0 inch high, and 1.0 inch wide, with 20 magnetic sections (magnets) 72 spaced 0.2 inches apart. The magnetic sections 72 are 0.04 inches thick and 0.75 inches high, with a width of 0.75 inches. The height and width of the magnetic sections 72 are determined as a function of the thickness of the magnetic sections 72. The magnetic poles of the magnetic sections 72 are alternated so that like poles of the spaced magnetic alternated so that like poles of the spaced magnetic sections 72 are facing each other. The slot 60 for receiving the dilatation catheter 38 is 0.10 inch wide and 0.10 inch deep. The holes 68 centered under each of the magnetic sections 72 (for gluing magnetic sections 72 in place during assembly) are approximately 0.04 inches in diameter.

Figure 9:
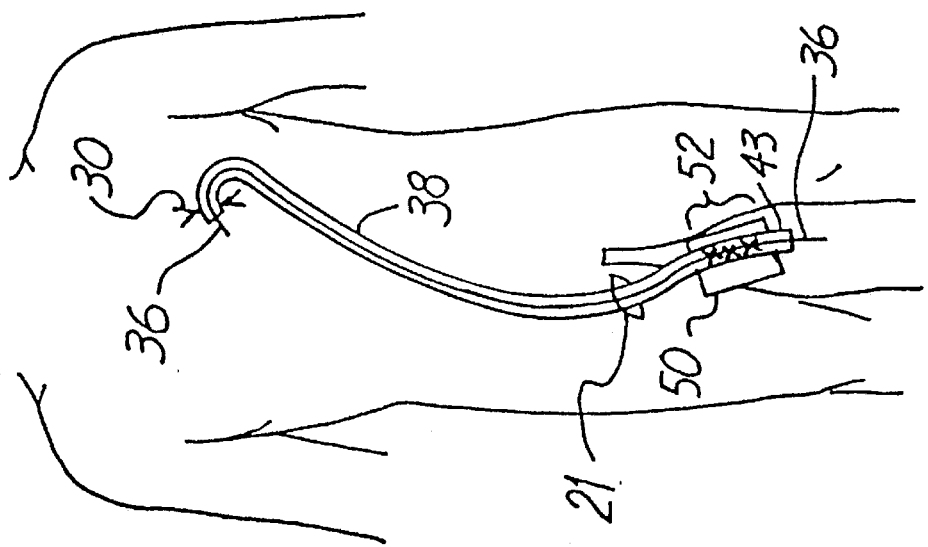
FIGS. 8–13 depict a preferred method of use for the present invention.
Figure 8:
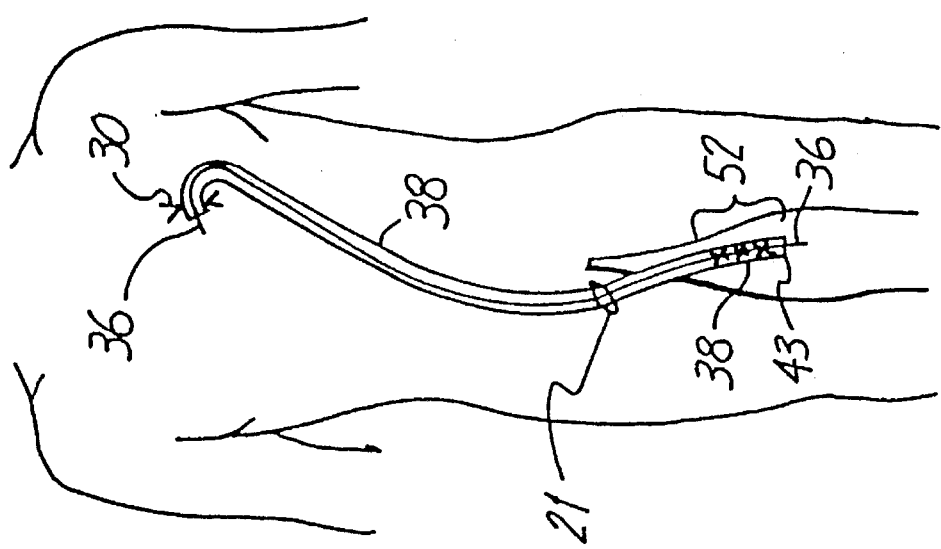

The device of the present invention for facilitating a dilatation catheter exchange while maintaining a guide wire in place within a vessel is employed in the following manner. Of course, performing such an exchange requires that the angioplasty catheter system 32 already be in place in the vascular system 20 of the patient as previously described. As such, the proximal end of the guide wire 36 and the proximal end 43 of the dilatation catheter 38 protrude proximally outside the patient as seen in FIG. 8, with the proximal end of the guide wire 36 extending proximally beyond the proximal end 43 of the dilatation catheter 38. Recall that the operative segment 52 of the guide wire 36 (identified schematically by the "xxx's" in FIGS. 8–13) is located near the proximal portion of the guide wire 36 and is disposed within the proximal end 43 of dilatation catheter 38. To begin the exchange, the physician grasps the proximal end of the guide wire 36 to maintain its distal end in place across the stenosis 30. The physician then places a proximal portion of the dilatation catheter 38 (having the operative segment 52 extending therein) into the slot 60 of the housing member 56 (see FIGS. 7 and 9) and aligns the operative segment 52 with the tool 50.

The alignment of the operative segment 52 with the tool 50 is relatively simple because the operative segment 52 is longer than the slot 60 in the tool 50, and the distance between the magnetically permeable sections 54 on the guide wire 36 and the corresponding magnetic sections 72 on the tool 50 is relatively small. The result is that when the operative segment 52 is positioned within the slot 60 of the tool 50 only a small amount of movement (less than half the distance between the magnetic sections 72 on the tool 50) is required to align the magnetically active portions of the operative segment 52 and the tool 50. As the spacing between the magnetic sections 72 becomes smaller, less movement is required to align the tool 50 and the operative segment 50. At the given dimensions, the tool 50 and the operative segment 52 effectively become self-aligning, and simply positioning the operative segment 52 within the slot 60 of the tool 50 ensures proper alignment.

Once the operative segment 52 on the guide wire 36 is properly aligned with the magnetic sections 72 of the captivation tool 50, the guide wire 36 is attracted to the captivation tool 50 by the resultant magnetic field created therebetween (see FIGS. 2, 3, and 7). This results in the guide wire 36 being pulled (along with the dilatation catheter shafts 41 and 42) against the bottom slot surface 66 of the housing member 56 as seen in FIGS. 3 and 7. The drawings are exaggerated for clarity in this regard.

Once the guide wire and tool 50 have been so coupled, the physician releases the guide wire 36 proximal to the tool 50 and then grasps the proximal end 43 of the dilatation catheter 38 proximally of the tool 50. The dilatation catheter 38 is pulled proximally over the guide wire 36 and past the tool 50 while holding the tool 50 (and thus the guide wire 36) in a stationary position relative to the patient (see FIG. 10). The physician may choose to hold the tool 50 in his hand, or alternately the physician may place the tool 50 on the table to hold the tool 50 stationary. The longitudinal magnetic attraction between the guide wire 36 and the captivation tool 50 is greater than the friction between the guide wire 36 and the inner catheter shaft 41. Accordingly, the dilatation catheter 38 may be pulled over the guide wire 36 while maintaining the guide wire 36 in the same position relative to the captivation tool 50. This ultimately maintains the guide wire 36 in position across the stenosis 30 during this maneuver, as long as the tool 50 is held generally stationary with respect to the patient.

Figure 11:
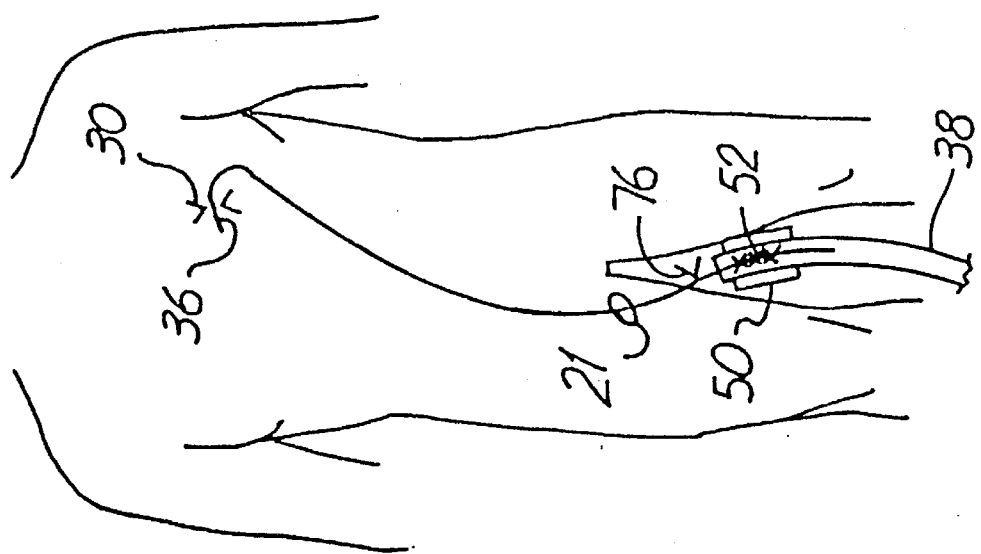
Figure 10:
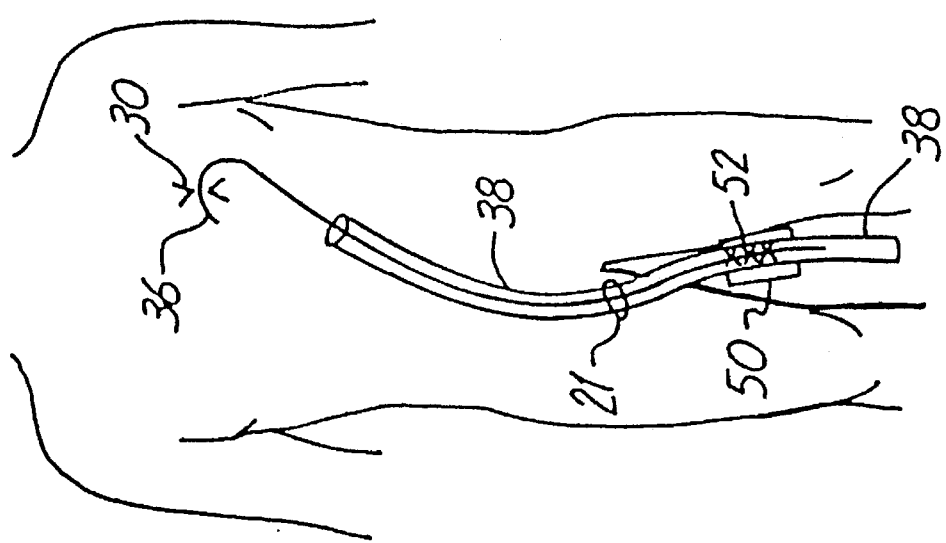
Figure 13:
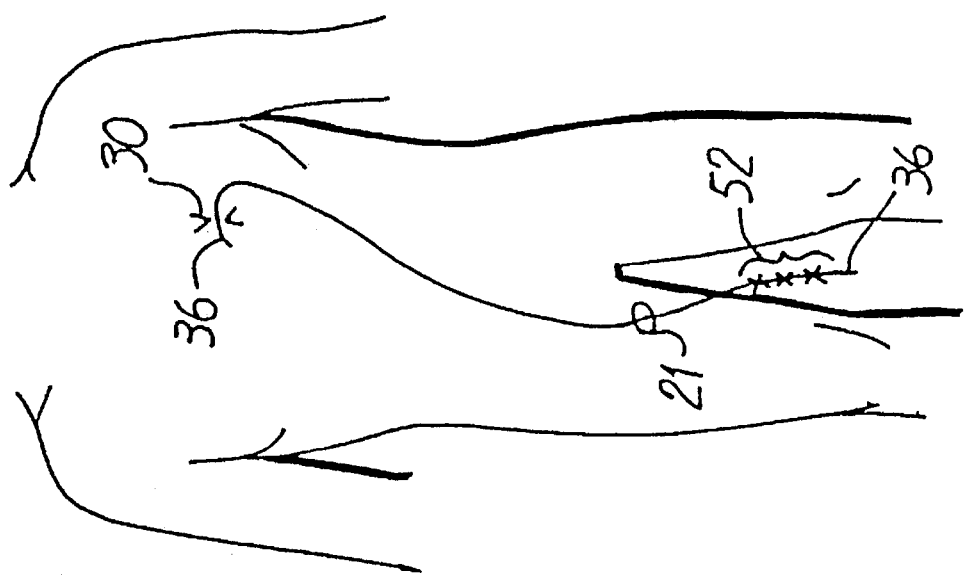

The catheter 38 is withdrawn until the distal end of the dilatation catheter 38 is exposed outside of the patient's body as seen in FIG. 11. As such, a portion of the guide wire 36 will be exposed between the distal end of the catheter 38 and the proximal end of the guide catheter 34, which protrudes outside the patient's body. The physician then grasps this exposed portion of the guide wire 36 distal to the tool 50 and the distal end of the dilatation catheter 38 as at 76. The physician then laterally separates the catheter 38 and the guide wire 36 therein from the tool 50 by overcoming the radial magnetic forces between the guide wire operative segment 52 and the tool 50. The physician then completely withdraws the first balloon catheter 38 proximally off of the guide wire 36. The guide wire 36 has thus been held in a generally stationary position during the entire catheter removal procedure in a very simple and elegant manner, which can be managed by the physician without the need for extra persons to hold or manipulate additional catheter or guide wire components.

Next, while still maintaining the guide wire 36 in place by grasping at 76, a second dilatation catheter is placed on the proximal end of the guide wire 36 and moved distally over the guide wire 36 until the operative segment 52 of the guide wire 36 is positioned within a distal end of the second dilatation catheter (preferably within the second catheter at a point proximal to the balloon thereon). The operative segment 52 of the guide wire 36 and the tool 50 are positioned together (as previously described) until the operative segment 52 is magnetically aligned with the magnetic sections 72 of the captivation tool 50. The physician then releases the guide wire 36 distally of the tool 50 as at 76, grasps the second dilatation catheter, and distally advances the second dilatation catheter over the guide wire 36 longitudinally relative to tool 50 and the guide wire 36 to distally advance the second catheter through the guide catheter 34. During dilatation catheter advancement, the captivation tool 50 is held stationary relative to the patient to ultimately maintain the distal end of the guide wire 36 in place across the stenosis 30. The second dilatation catheter is advanced distally over the guide wire 36 until the proximal end of the guide wire 36 extends beyond a proximal end of the second dilatation catheter. The physician then grasps the guide wire 36 proximal to the tool 50 and dilatation catheter manifold 44, and separates the second dilatation catheter and the guide wire 36 therein from the tool 50. The second dilatation catheter is then further advanced distally over the guide wire 36 until the balloon of the second dilatation catheter is across the stenosis 30 for dilatation. The dilatation catheter exchange procedure using the captivation tool 50 and operative segment 52 can thus be repeated in this manner as necessary.

During the dilatation catheter removal and insertion procedure, the position of the guide wire 36 is maintained relative to the guide catheter 34, and more importantly, relative to the stenosis 30. The present invention is ideally suited for facilitating catheter exchanges without the need for a long exchange guide wire, a modified catheter, or additional intravascular devices such as a guide wire holding balloon for "trapping" the guide wire against a wall of the guide catheter. The present invention allows catheter exchanges over a standard length guide wire using a catheter having a full length guide wire lumen. Additionally, the procedure may be performed by a single physician and without the prolonged use of X-ray fluoroscopy used to observe the position of the guide wire, since the guide wire is held stationary by use of the present invention and thus its position need not be continuously observed.

Figure 12:
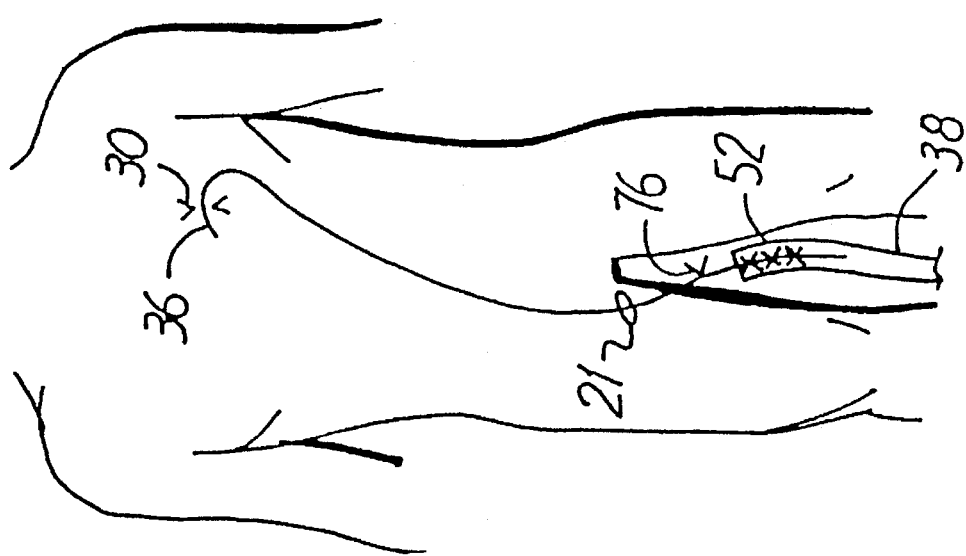

The utility of the present invention is not limited to catheter exchange procedures. The present invention may be used as a "third hand" during a catheterization procedure. Typically during a catheterization procedure, the physician is required to simultaneously manipulate the guide wire 36, the dilatation catheter 38, and the guide catheter 34. The simultaneous manipulation often requires the use of additional medical personnel, which increases the cost and complexity of the procedure. By placing the operative segment 52 adjacent the tool 50 and securing the tool 50 itself in a stationary position, the present invention eliminates the need for the physician (or a second person) to continually hold the guide wire 36 during the procedure. The operative segment 52 provided on the guide wire 36 can be made long enough to allow the use of more than one tool 50 during a catheterization procedure. For example, when the physician is withdrawing the dilatation catheter 38 from the patient and is required to grasp the guide wire 36 before completely removing the dilatation catheter 38 from the guide wire 36 (e.g., when the physician grasps the guide wire 36 at 76 before completely withdrawing the dilatation catheter 38 of the guide wire 36, as seen in FIGS. 11 and 12 and as previously described), a second tool 50 may be used in place of the physician actually grasping the guide wire 36.

Figure 21:
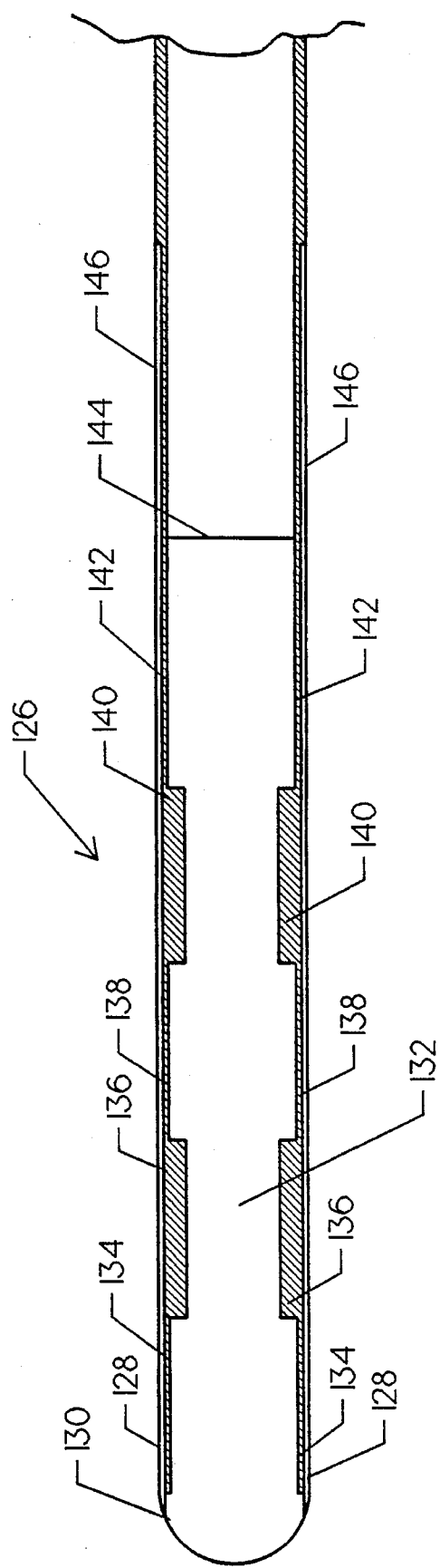
FIG. 21 is a longitudinally sectioned view of the proximal end of the guide wire of the preferred embodiment.

In alternate embodiments, the operative segment 52 on the guide wire 36 may take a number of forms including those shown in FIGS. 14, 15 and 21. In FIG. 14, each of a plurality of non-magnetically permeable segments 58 are secured about reduced diameter portions 55 of the guide wire 36A. The guide wire 36A is made of a magnetically permeable material, and segments 58 are a non-magnetically permeable material such as plastics or non-magnetic metals. As seen in FIG. 15, the operative segment 52 may include an elongate non-magnetically permeable tubular member 51 with a plurality of solid cylindrically-shaped magnetically permeable segments 54A secured within member 51. The tubular member 51 is connected to a reduced diameter portion 59 of the guide wire 36. Another embodiment of the operative segment 52 is a guide wire segment made of a single material which can exist in either a magnetic or non-magnetic state (such as martensite of austenite steel) depending upon the heat treatment of the material. Alternating sections of the wire are heat treated locally to form alternating magnetic and non-magnetic sections on the guide wire. In each embodiment of the operative segment 52, the magnetically permeable material may be replaced with permanent magnets.

Figure 16:
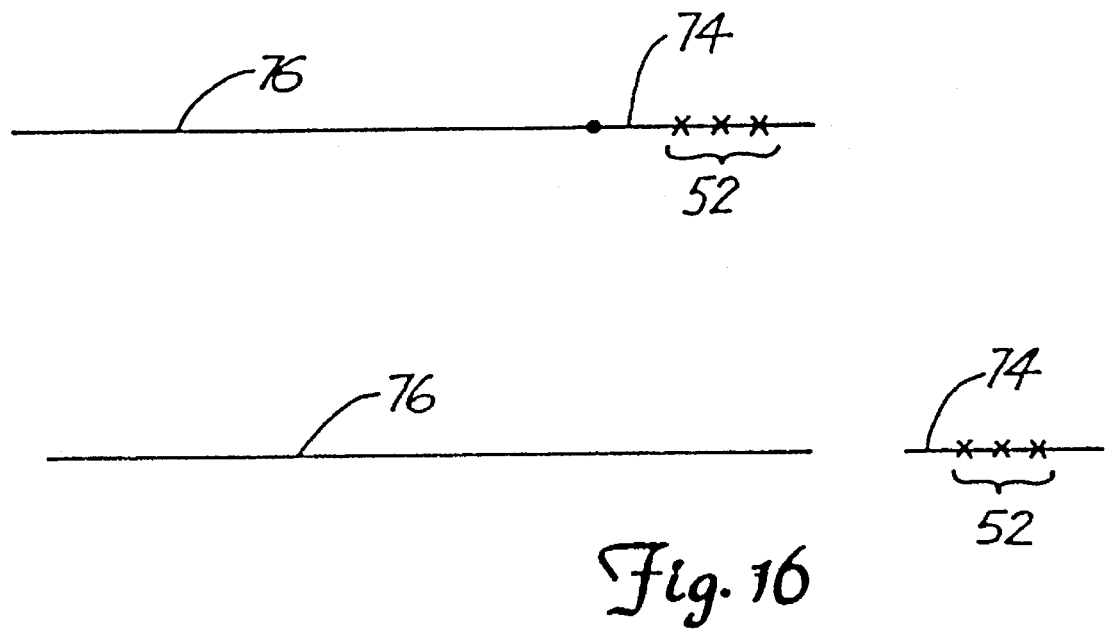
FIG. 16 is a schematic illustration of a guide wire extension containing an operative segment.

The operative segment 52 may be provided on a short guide wire extension 74 (e.g., about 12 inches long) for a standard guide wire. As shown schematically in FIG. 16, this short extension 74 would connect to the proximal end of the standard guide wire 76 in a conventional manner, such as shown, e.g., in Gambale et al. U.S. Pat. No. 4,922,923; Messner et al. U.S. Pat. No. 4,875,489; Crittenden et al. U.S. Pat. No. 5,035,686; or Palmer et al. U.S. Pat. No. 5,117,838. The short extension 74 is selectively attachable to the standard guide wire 76 and can be connected and disconnected multiple times during a single procedure. Use of the short guide wire extension 74 with an operative segment 52 allows the physician to perform a catheter exchange using the present invention even if the catheterization procedure was started using a standard guide wire 76. The use of the short extension 74 in a catheter exchange merely requires the additional acts of attaching the extension 74 to the guide wire 76 and withdrawing the original catheter proximally far enough to cover the operative segment 52 on the short extension 74 before positioning the dilatation catheter 38 relative to the tool 50 for magnetic coupling of the extended guide wire and the tool 50. Otherwise, the use of such a short guide wire extension 74, either for holding the wire/catheter assembly during the procedure or to facilitate a catheter exchange over a stationary wire, is essentially the same as described herein.

The tool 50 may be adapted to fit over the guide catheter 34 (as in a 2-piece "clam shell" design), may be made in the form of a guide catheter extension, or may be incorporated directly into the guide catheter Y-adaptor 37, for example. Additionally, the tool 50 may be designed such that the magnetic sections 72 in the tool 50 are moved within the housing member 57 and away from the slot 60 in the housing member 56. With this feature, the attraction between the tool 50 and the operative segment 52 on the guide wire 36 is effectively "turned off" when the magnetic sections 72 are moved sufficiently laterally away from the slot 60 in the housing member 56 and the operative segment 52 of the guide wire 36 therein to break the magnetic attraction therebetween.

Figure 18:
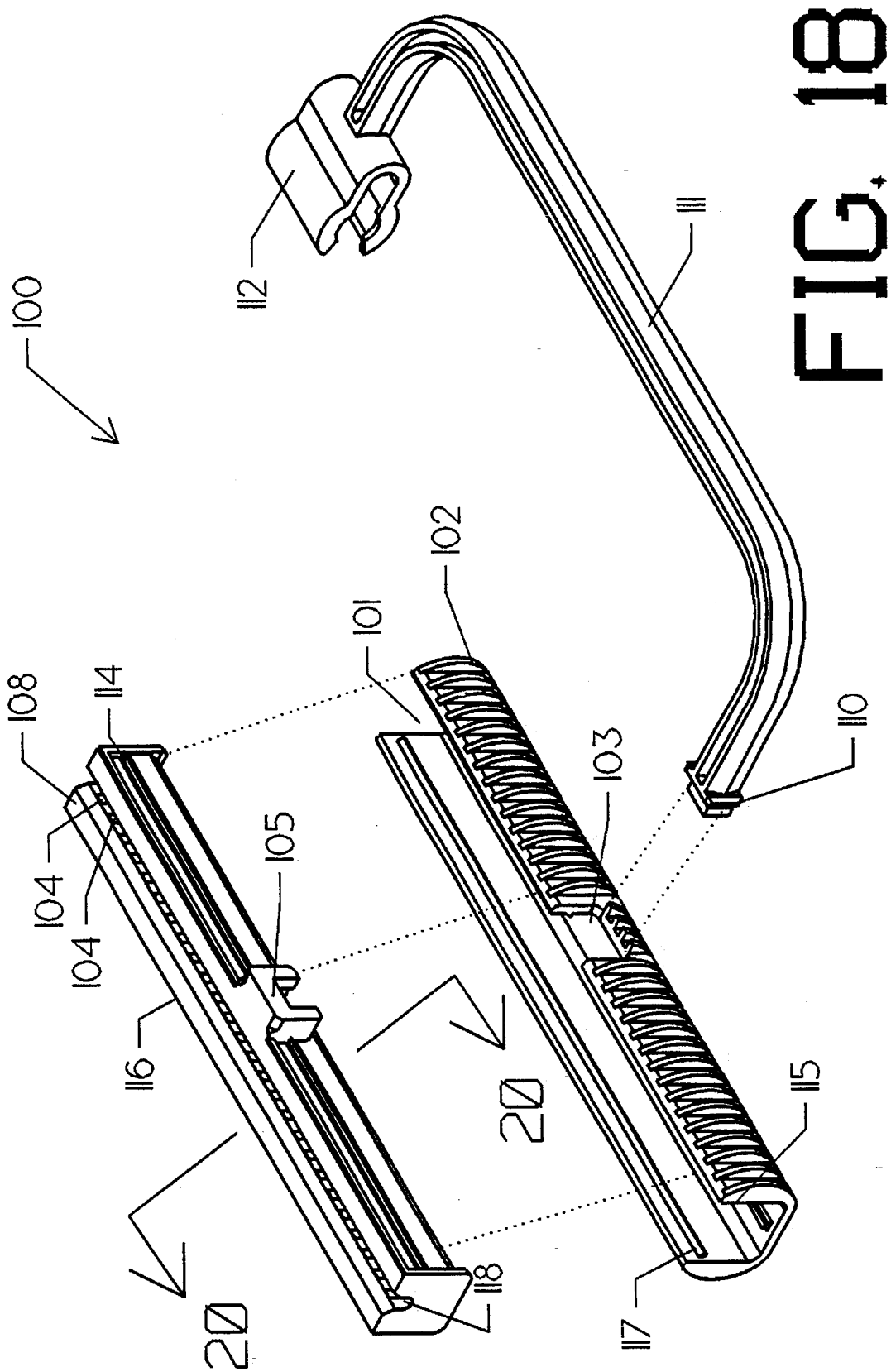
FIG. 18 is an exploded view of the three major components of the tool of an alternative embodiment.

The three major components of an alternative embodiment of the tool are shown in exploded view 100 in FIG. 18. Magnet fixture block 108 receives permanent magnets (not shown) in magnet receiving slots 104 as described above. Preferably, the magnets are placed with alternating polarity to increase the effective axial holding force and decrease the effective normal force which reduces longitudinal friction. Magnet fixture block 108 is preferably molded of a polycarbonate, with General Electric Lexan HP2X-42046 being the recommended material.

Bottom block 102 is molded of a similar but clear material, such as General Electric Lexan HP2X-111, and engages with magnet fixture block block 108, through receiving channel 101. In operation, magnet fixture block 108 is held within receiving channel 101 by the engagement of longitudinal protrusions 116 and 114 of magnetic fixture block 108 within longitudinal channels 115 and 117 of bottom block 102, respectively. Configured catheter receiving notch 118 stabilizes the position of the catheter assembly as discussed in greater detail below.

Operator handle 111 is molded of Lexan HP2X-111 (clear) material. It has a catheter receiving element 112 and a configured engagement latch 110, which is fixedly engaged within receiving notch 103 of bottom block 102 and receiving notch 105 of magnet fixture block 108.

Figure 19:
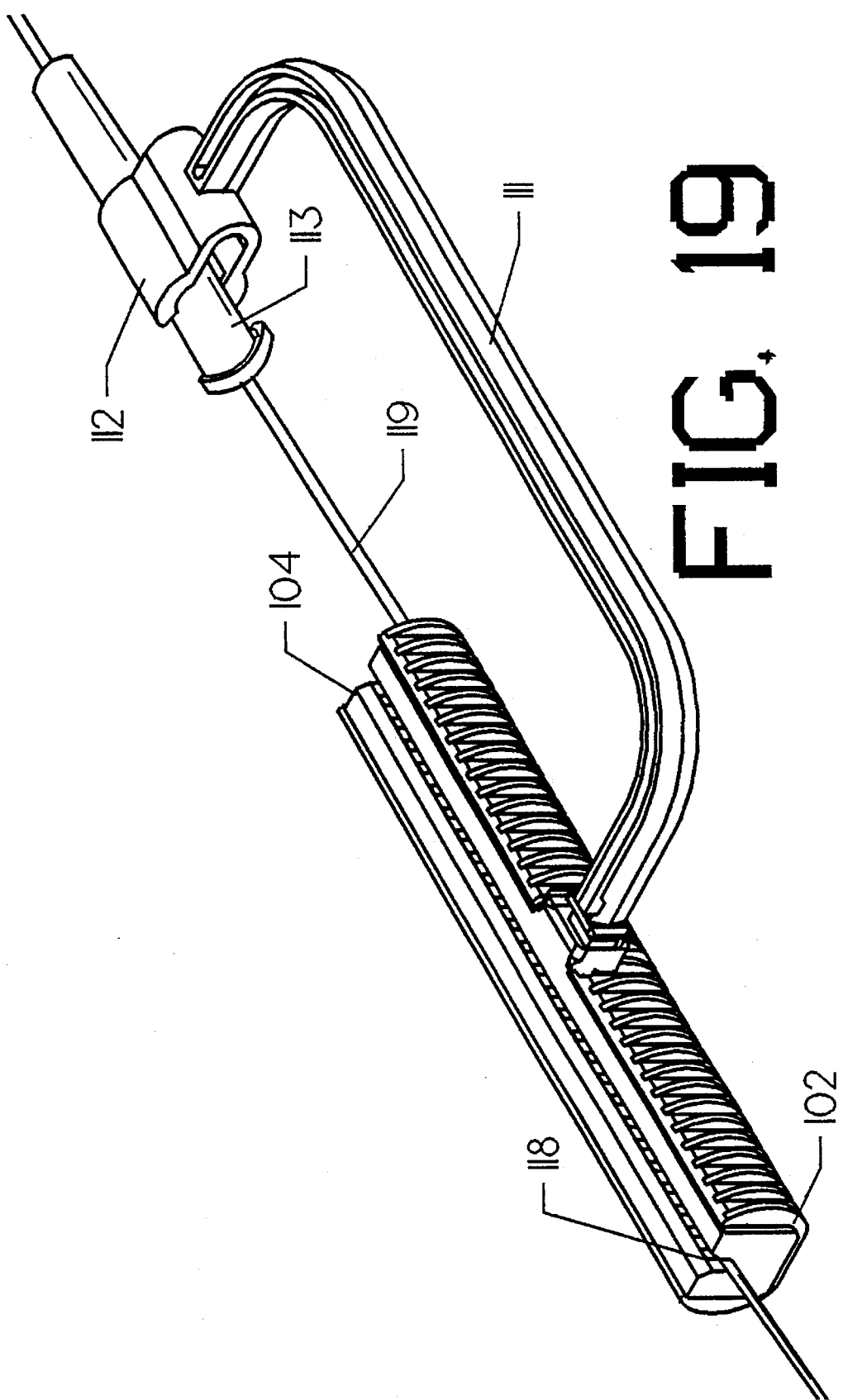
FIG. 19 is an isometric view of the operation of the alternative embodiment of FIG. 18.

FIG. 19 is a isometric composite view of the alternative embodiment of FIG. 18 in operation. Catheter receiving element 112 slidably engages y-adapter 113 of catheter assembly 119 as shown. Catheter assembly 119 is stabilized within configured catheter receiving notch 118. The operator conveniently grasps the entire assembly using handle 111.

Figure 20:
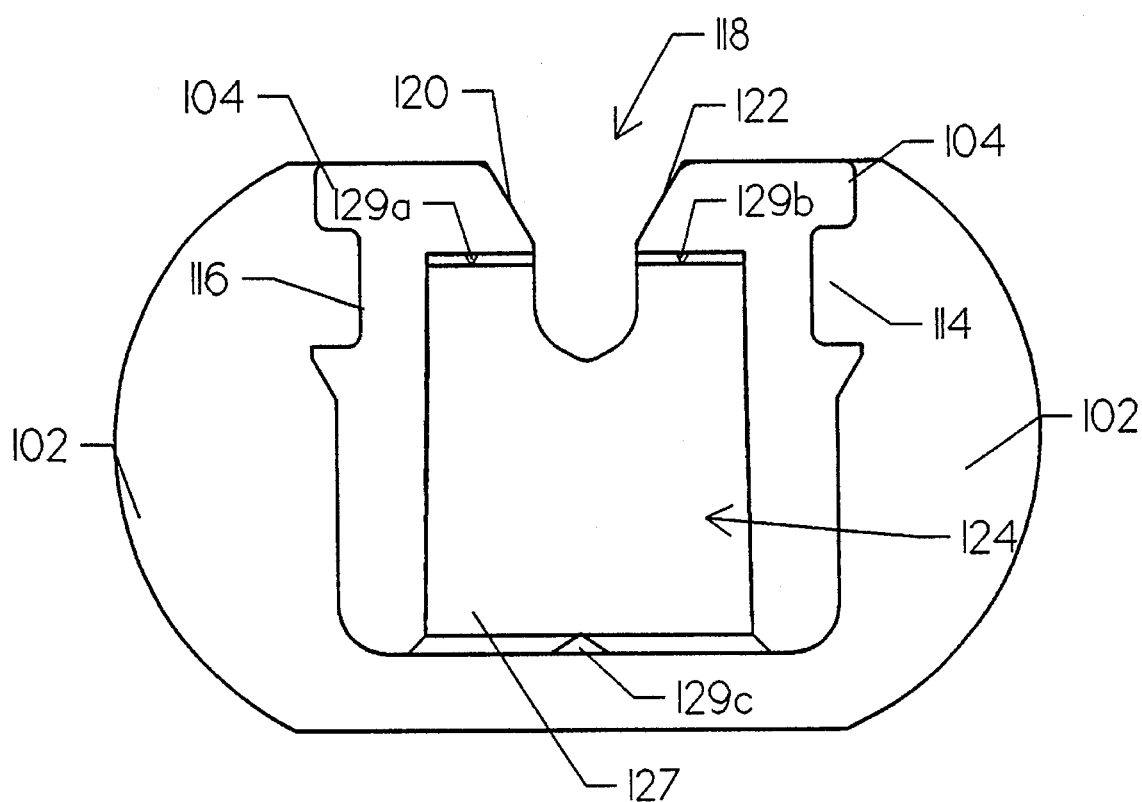
FIG. 20 is a close up view of the catheter receiving notch of the alternative embodiment.

A cross sectional view of the assembled tool is shown in FIG. 20. Inclines 120 and 122 direct catheter assembly 119 into catheter stabilization channel 118, which is configured to hold catheter assembly 119 within the above described magnetic field. Permanent magnet 127 is shown held in place by contact with molded spikes 129a, 129b, and 129c.

An alternative embodiment of the proximal end of guide wire active area 126 is shown in longitudinal sectioned view 21. The inner core 132 of the assembly is preferably a wire of Hyperco 50B, which is an alloy of 48.5% cobalt, 48.5% iron, and 3% vanadium. It is commercially available as explained above and has a diameter of about 0.011 inch.

Inner core 132 is circumferentially ground to produce a reduced diameter of about 0.0045 inch for a distance of about 0.075 inch at areas 136 and 140, which are separated by distance 138, also about 0.075 inch. Proximal distance 134 is about 10.075 inches, and distance 142 is about 0.5 inch. The proximal end of a standard spring coil guide (not shown for clarity) is butt welded to distal end 144 of inner core 132.

Inner core 132 is coated with an adhesive, which is preferably Hysol 9412 to fill the ground areas 136 and 140 to an overall depth at the unground areas of about 0.001 inch. The resulting structure has a uniform outside diameter of about 0.011 inch, which is covered before curing is completed by hypotubing 128 of 304 stainless steel. The wall thickness of hypotubing 128 is chosen to provide a standard finished outside diameter, such as 0.018 or 0.014 inch. Hypotubing 128 extends distally of distal end 144 of inner core 132 by at least 0.5 inch along area 146 to provide strain relief to the butt weld at distal end 144. Proximal end 130 is ground to a smooth hemispherical shape.

Figure 17:
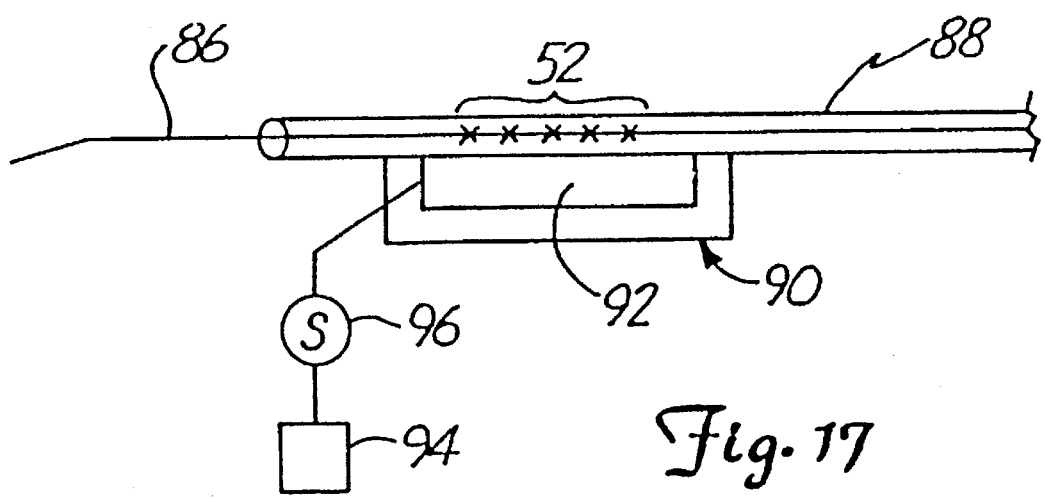
FIG. 17 is a schematic illustration of a tool which includes an electromagnet.

Another way to selectively apply a magnetic field between the operative segment of the guide wire and the tool is to form the magnet on the tool as an electromagnet. As illustrated diagrammatically in FIG. 17, a guide wire (or guide wire extension) 86 includes an operative segment 52 (as previously described) and the guide wire 86 is, in use, inserted within a lumen of a catheter 88. A tool 90 in this embodiment includes an electromagnet 92 which has selectively activated sections therein aligned to cooperate within the operative segment 52, and which is connected to a current source 94 through an on/off switch 96. Operation of the switch 96 thus controls the application of current to the electromagnet 92 and the creation of a magnetic field thereby. The selectively activated sections within the tool 90 may be energized by wall current (AC) or rectified wall current (DC), either of which can be turned off by switch 96 to break the holding force between the tool 90 and the guide wire 86.

It is also contemplated that alternate forms of coupling forces may be used in the present invention. For instance, instead of using permanent magnets or electromagnets, the coupling force field between the guide wire and the captivation tool may be generated by the use of electrostatic or electric fields. In each case, the coupling force between the tool and the guide wire can operate through the catheter body, and there is no contact required between the tool and the guide wire.

Although the present invention has been described with reference to preferred embodiments, workers skilled in the art will recognize that changes may be made in form and detail without departing from the spirit and scope of the invention.

What is claimed is:

1. An apparatus for cooperating with a catheter assembly, the assembly including a catheter having a longitudinal lumen and a shaft insertable in the lumen, comprising:

a. a housing for holding a proximal end of the catheter assembly against lateral motion, the housing having a longitudinal catheter receiving groove therein, the groove having a proximal end and a distal end and a longitudinally extending side opening therebetween through which the proximal end of the catheter can be placed into the groove; and b. be a device for generating a differential holding force within the housing capable of preventing longitudinal motion of the shaft of the catheter assembly while allowing longitudinal motion of the catheter.

2. An apparatus according to claim 1 further comprising an operator handle fixedly attached to the housing.

3. An apparatus according to claim 2 wherein the operator handle further comprises a coupler for slidable attachment to the catheter assembly.

4. An apparatus according to claim 1 wherein the shaft is a guide wire and the catheter is slidably located over said guide wire.

5. An apparatus according to claim 4 wherein the guide wire has a distal end and a proximal end and wherein the proximal end of the guide wire includes an active area which is prevented from longitudinal motion by the device.

6. A tool, comprising:

a housing including an elongated block having a longitudinal channel therein;

an elongated second block held in the channel, and having a groove configured to receive a catheter having a longitudinal lumen with a guide wire having an operable portion slidably placed in the lumen; and a permanent magnet retained between the first and second blocks so that the operable portion of the guide wire can be held by a magnetic field created by the magnet.

7. A tool in accordance with claim 6, wherein the magnet is a permanent magnet.

8. A tool in accordance with claim 7, comprising a plurality of spaced apart permanent magnets configured to correspond with a plurality of spaced apart magnetically permeable portions of the operable portion of the guide wire.

9. A tool in accordance with claim 7, wherein the magnets are spaced apart by a uniform distance.

10. A tool in accordance with claim 7, wherein the polarity of every other magnet is reversed.

11. The tool in accordance with claim 6, further comprising a handle operably connected to the housing at a first end and including a catheter receiving element at a second end.

12. The tool in accordance with claim 11, wherein the catheter receiving element is configured to engage with a Y-adaptor operably connected to the catheter.

13. A catheter in accordance with claim 12, wherein the handle extends generally parallel to the groove and the adaptor is configured to hold the Y-adaptor in an approximately longitudinal axial alignment with the groove.

14. A tool in accordance with claim 13, wherein the first block, second block and handle are molded polycarbonate.

* * * * *